US010251916B2

(12) United States Patent
Kuramoto et al.

(10) Patent No.: US 10,251,916 B2
(45) Date of Patent: Apr. 9, 2019

(54) CELL COMPOSITION FOR TREATMENT OF UTERINE TISSUE AND METHOD FOR PRODUCING SAME

(71) Applicant: Tokyo Women's Medical University, Shinjuku-ku (JP)

(72) Inventors: Goro Kuramoto, Shinjuku-ku (JP); Soichi Takagi, Shinjuku-ku (JP); Tatsuya Shimizu, Shinjuku-ku (JP); Teruo Okano, Shinjuku-ku (JP)

(73) Assignee: TOKYO WOMEN'S MEDICAL UNIVERSITY, Shinjuku-ku (JP)

( * ) Notice: Subject to any disclaimer, the term of this patent is extended or adjusted under 35 U.S.C. 154(b) by 1 day.

(21) Appl. No.: 15/134,738

(22) Filed: Apr. 21, 2016

(65) Prior Publication Data

US 2016/0310543 A1    Oct. 27, 2016

(30) Foreign Application Priority Data

Apr. 21, 2015   (JP) .................................. 2015-086932

(51) Int. Cl.
| | | |
|---|---|---|
| *A61L 27/38* | (2006.01) | |
| *A61K 35/36* | (2015.01) | |
| *A61K 35/48* | (2015.01) | |
| *C12N 5/071* | (2010.01) | |
| *A61K 35/35* | (2015.01) | |

(52) U.S. Cl.
CPC .............. *A61K 35/48* (2013.01); *A61K 35/35* (2013.01); *A61K 35/36* (2013.01); *C12N 5/0682* (2013.01); *C12N 5/0697* (2013.01); *C12N 2500/25* (2013.01); *C12N 2500/38* (2013.01); *C12N 2501/11* (2013.01); *C12N 2501/385* (2013.01); *C12N 2501/39* (2013.01)

(58) Field of Classification Search
None
See application file for complete search history.

(56) References Cited

U.S. PATENT DOCUMENTS 7,049,057 B2 *   5/2006   Atala ...................... A61L 27/18
435/1.1

FOREIGN PATENT DOCUMENTS

| CN | 101121043 A | 2/2008 |
|---|---|---|
| JP | 2005-176812 | 7/2005 |
| JP | 2007-525231 | 9/2007 |
| WO | 2012/036246 A1 | 3/2012 |

OTHER PUBLICATIONS

Agarwal et al "Elevated Temperature Degradation of a 50:50 Copolymer of PLA-PGA" Tissue Engineering, 1997, vol. 3, No. 4, pp. 345-352. (Year: 1997).*
Arnold et al "Endometrial stromal cells regulate epithelial cell growth in vitro: a new co-culture model" Human Reproduction, 2001, vol. 16, No. 5 pp. 836-845. (Year: 2001).*
Cerqueira et al "Cell sheet technology-drive re-epithelialization and neovascularization of skin wounds" Acta Biomaterialia, 2014, vol. 10 pp. 3145-3155. (Year: 2014).*
Haraguchi et al, Nature Protocols, 2012, vol. 7, No. 5, pp. 850-858. (Year: 2012).*
Takagi et al "Reconstruction of functional endometrium-like tissue in vitro and in vivo using cell sheet engineering" Biochem Biophys Res Comm, 2014, vol. 446, pp. 335-340. (Year: 2014).*
Machine Translation of CN 101121043A (Year: 2008).*

* cited by examiner

*Primary Examiner* — Allison M Fox
(74) *Attorney, Agent, or Firm* — Oblon, McClelland, Maier & Neustadt, L.L.P.

(57) ABSTRACT

An object of the present invention is to provide a cell composition for treatment of uterine tissue that heals damage occurring in uterine tissue, including intrauterine adhesion, to a state that enables pregnancy. In addition, an object of the present invention is to provide a method for producing this cell composition for treatment of uterine tissue, and a cell composition for treatment of uterine tissue produced according to that method. The cell composition, which has a first cell layer containing epithelial cells and a second cell layer containing stromal cells, and the first cell layer is laminated on the second cell layer, has the ability to heal damage occurring in uterine tissue, including intrauterine adhesion, and restore it to a state that enables pregnancy.

5 Claims, 12 Drawing Sheets

FIG. 2
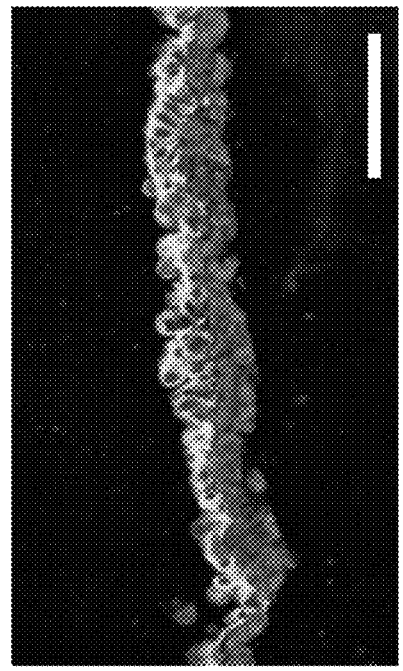
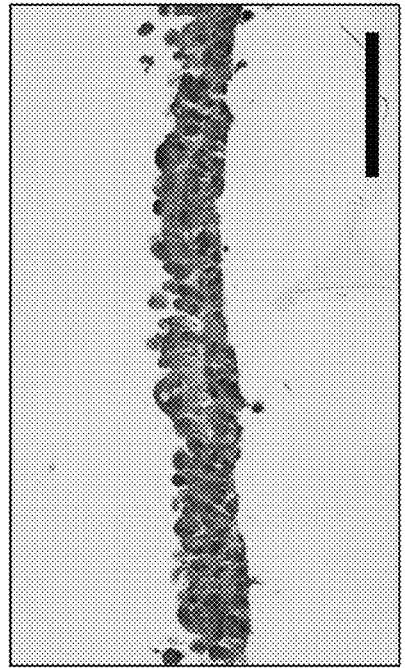
RED: VIMENTIN
GREEN: CK18
BLUE: NUCLEUS

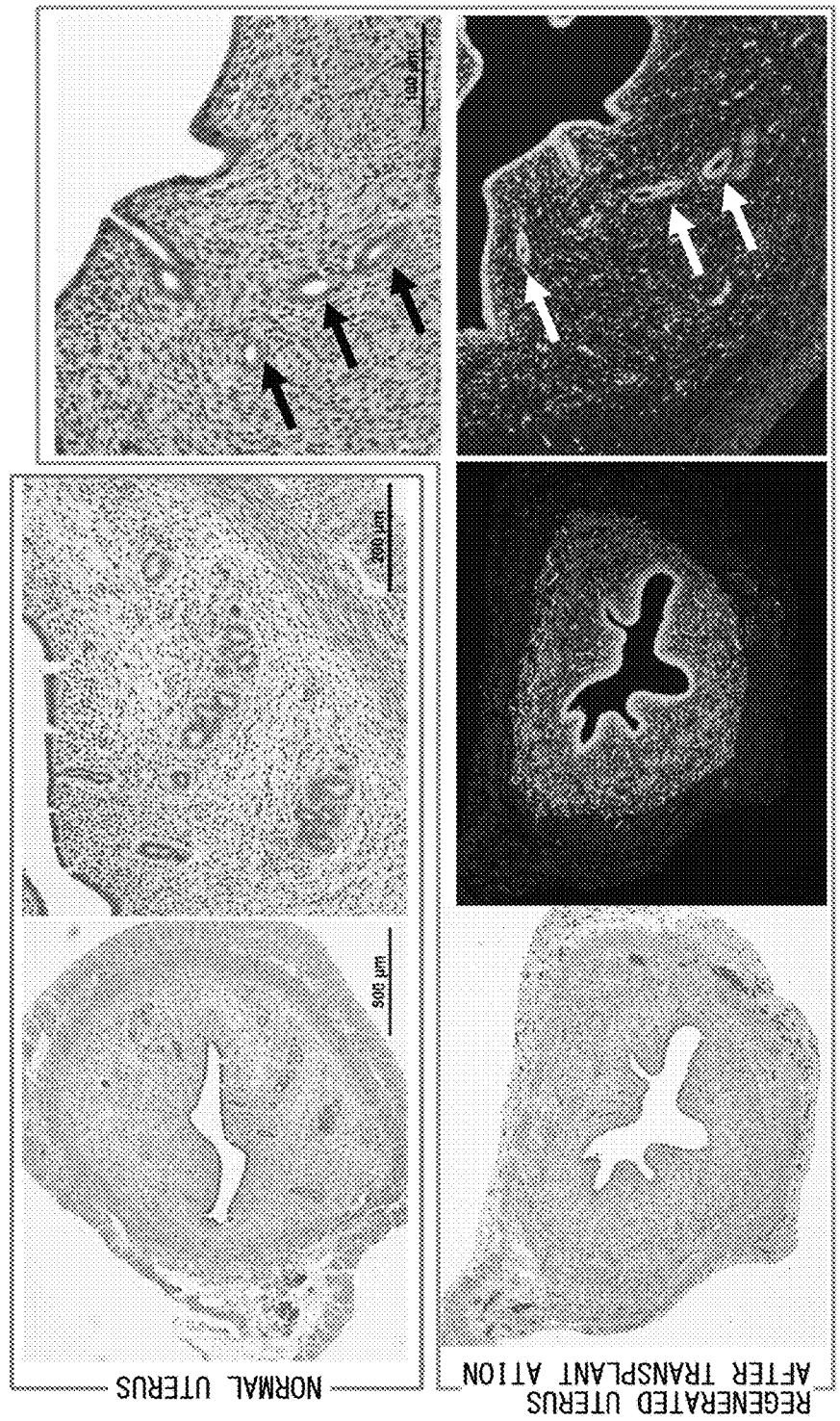

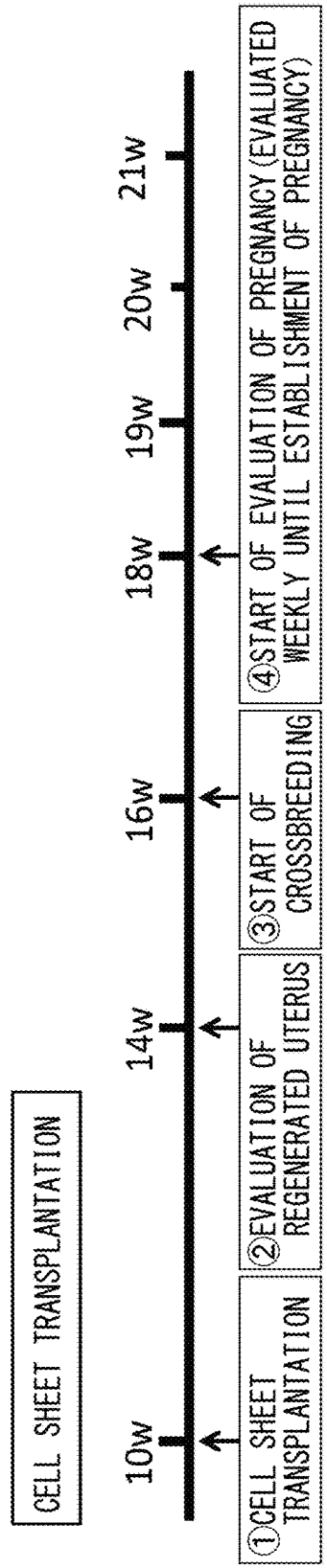

FIG. 4

PROTOCOL OF A CELL SHEET TRANSPLANTATION AND CROSSBREEDING

① CELL SHEET TRANSPLANTATION
② EVALUATION OF REGENERATED UTERUS
③ START OF CROSSBREEDING
④ START OF EVALUATION OF PREGNANCY (EVALUATED WEEKLY UNTIL ESTABLISHMENT OF PREGNANCY)

PRODUCING OF AN ENDOMETRIAL DEFECT MODEL:
ENDOMETRIAL FULL-THICKNESS RESECTION (A RANGE OF OF 1cm IN THE CENTER OF THE UTERUS).
① TRANSPLANTATION OF CELL SHEET:
A SINGLE EPITHELIAL CELL SHEET AND TWO STROMA CELL SHEETS WERE LAYERED AND TRANSPLANTED.
② EVALUATION OF REGENERATED UTERUS:
4WEEKS AFTER TRANSPLANTATION. ENDOMETRIAL THICKNESS WAS MEASURED BY ULTRASOUND.
UTERUS WAS EXTRACTED AND EVALUATED MACROSCOPICALLY AND HISTOLOGICALLY.
③ START OF CROSSBREEDING:
MATING WITH NORMAL MALE NUDERAT.
④ EVALUATION OF PREGNANCY:
CONFIRMATION OF AN ESTABLISHMENT OF PREGNANCY BY ULTRASOUND 2 WEEKS AFTER MATING.
AND CONFIRMATION AND RESECTION OF GESTATIONAL SAC BY LAPAROTOMY AFTER FETAL
HEART MOVEMENT BY ULTRASOUND.
MATING CONTINUING OR CHANGING IF UNABLE TO CONFIRM ESTABLISHMENT OF PREGNANCY.

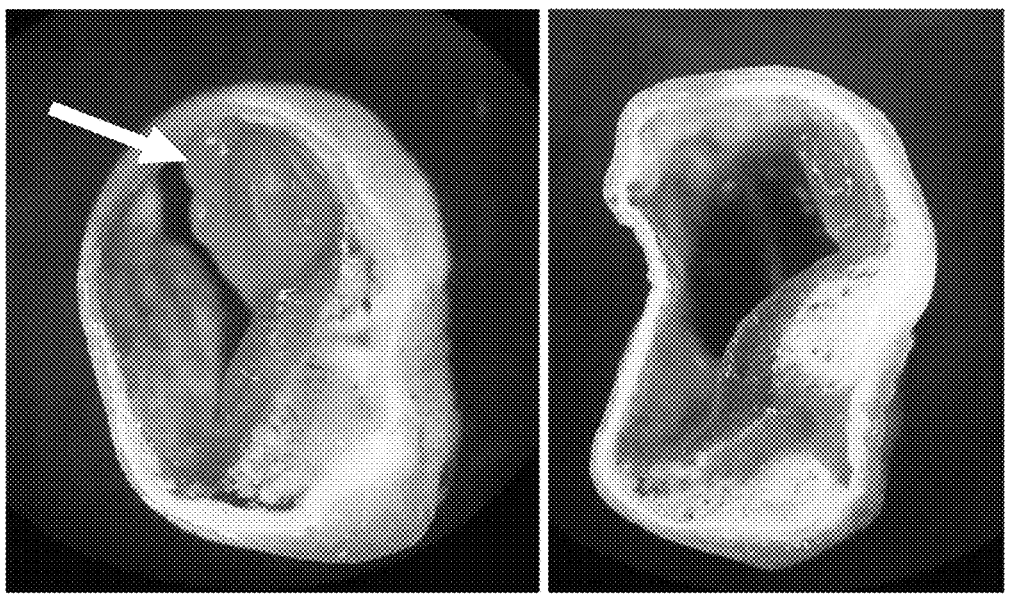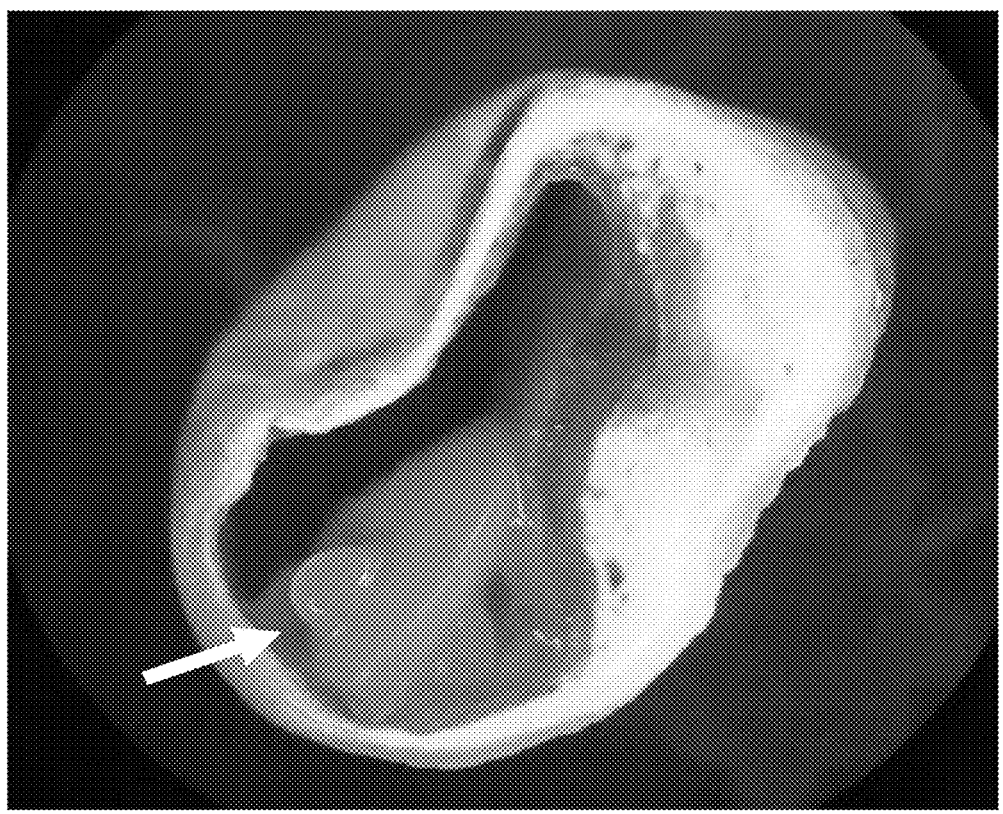
FIG. 6

FIG. 11
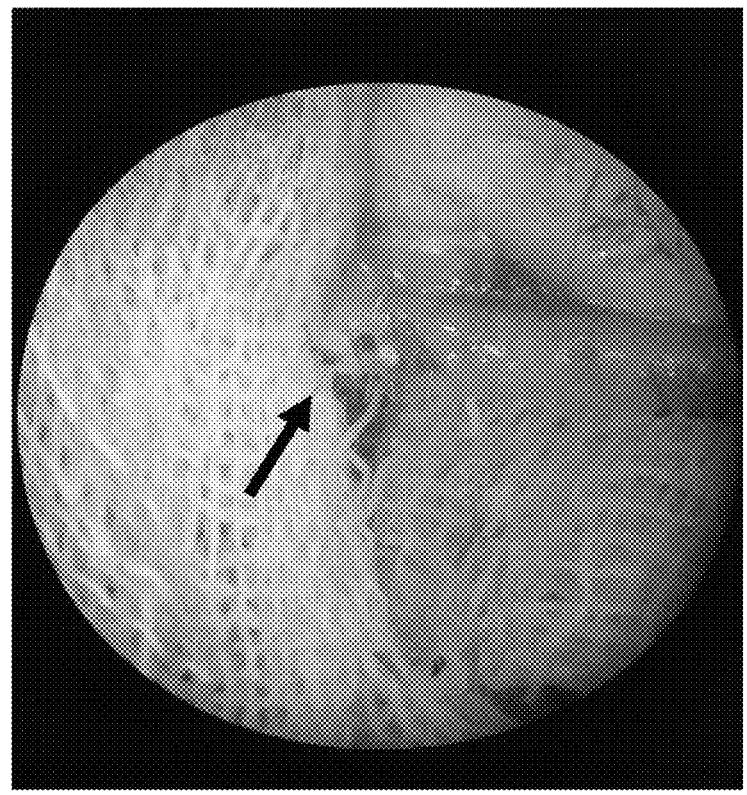
(B) TUBE FIXATION BY SUTURE
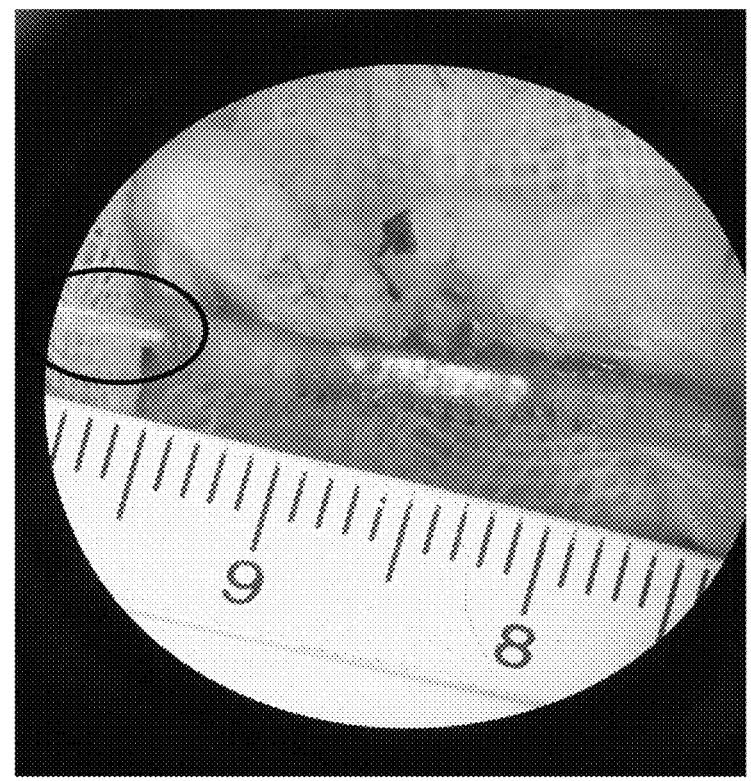
(A) FULL-THICKNESS DEFECT, APPROX 10mm

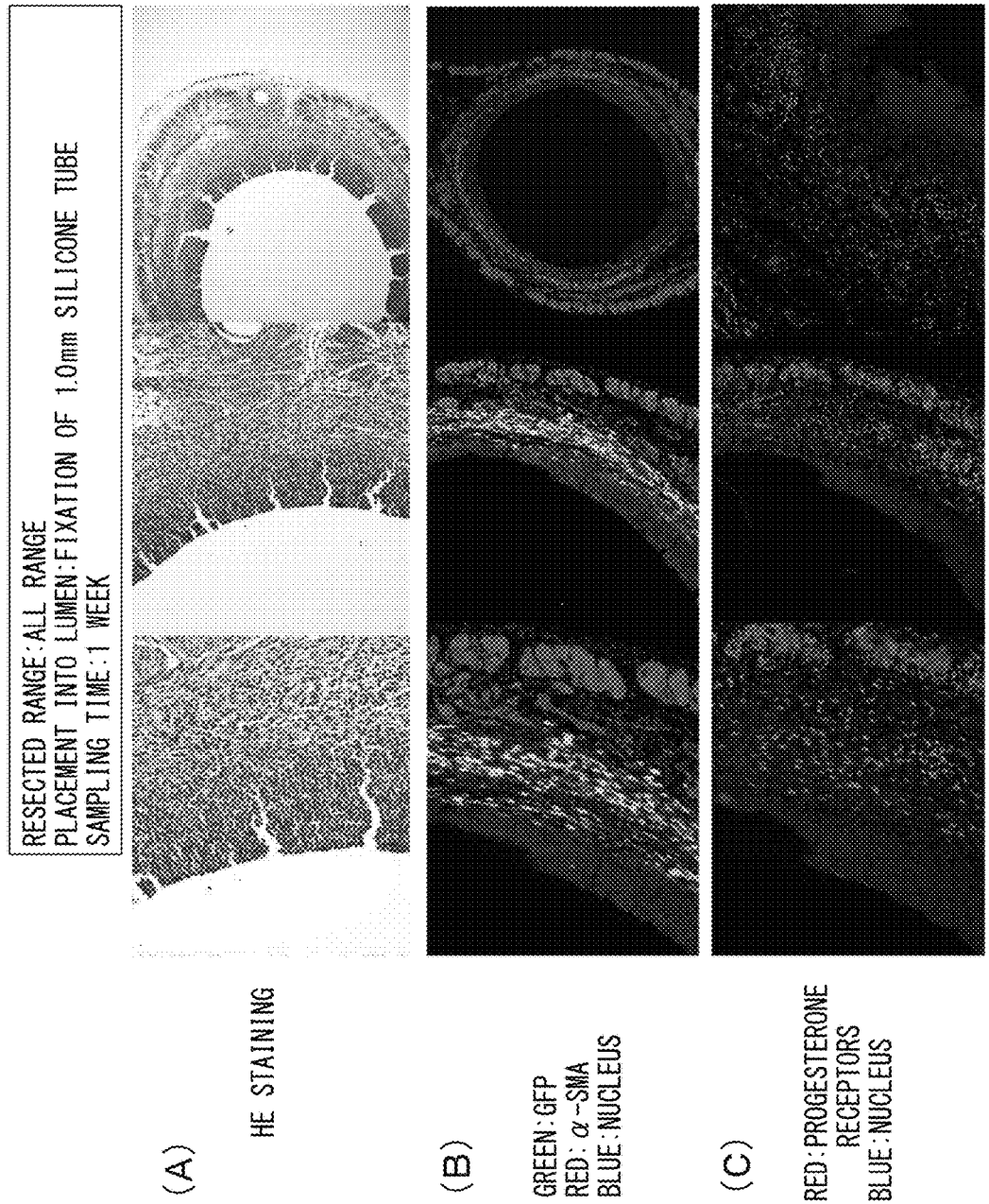

CELL COMPOSITION FOR TREATMENT OF UTERINE TISSUE AND METHOD FOR PRODUCING SAME

CROSS-REFERENCE TO RELATED APPLICATION

This application is based on and claims the benefit of priority to Japanese Application No. 2015-086932, which was filed on Apr. 21, 2015.

TECHNICAL FIELD

The present invention relates to a cell composition for treatment of uterine tissue. In addition, the present invention relates to a method for producing a cell composition for treatment of uterine tissue.

BACKGROUND ART

In the fields of obstetrics and gynecology, diseases have an effect on pregnancy for various reasons. There is the potential for the onset of an obstetric disease even after having become pregnant, and this may lead to a course of pregnancy that deviates from normal. Due to the effect of more women getting married at a later age attributable to the growing advance of women in society in recent years, there is considerable concern over an increase in the number of late-in-life pregnancies that are susceptible to complication by various obstetric diseases. On the other hand, since pregnancy rates are decreasing with the rise in the age at which women become pregnant, the problem of infertility is also occurring. Although the causes of infertility are categorized into those attributable to men and those attributable to women, those factors attributable to women are further categorized into such factors as ovulation factors, Fallopian tube factors, uterocervical factors or immunological factors. Although assisted reproductive technology (ART) is prominently used to treat this infertility and tremendous progress is being achieved, on the other hand, there is currently little progress being made with respect to other infertility treatment.

Infertility due to uterine factors is said to be caused by changes in the uterine cavity and endometrium. A disease known to be associated with adhesion or degeneration of the uterine cavity is intrauterine adhesion (Asherman's syndrome or IUA) caused by such factors as intrauterine curettage following miscarriage, uterine endoscopic surgery or uterine retained. Although the current method used to treat this intrauterine adhesion consists of surgically synechiotomy or preventing re-adhesion by administration of a hormone preparation following surgery or using an intrauterine device (IUD), there is the problem of frequent recurrence of adhesion. At present, there is no definitive treatment method for such diseases.

IUA causes infertility and menstrual disorders including amenorrhea. Although a study of whether or not patients thought to have IUA can become pregnant without receiving treatment confirmed that 46% of the patients became pregnant, only 30% of the pregnant women achieve term delivery, and placenta accreta was occurred in 13% of the cases (Non-Patent Document 1). Other reports have indicated that placenta accreta occurs in 5% to 31% of such cases. In this manner, IUA has an effect on obstetric complications during pregnancy in addition to infertility and menstrual disorders. Since there are cases in which curettage surgery, which is a cause of endometrial disorders, is unavoidable with respect to postpartum retained placenta and miscarriage surgery, adhesion is considered to occur with a certain probability. Standard treatment for this disease consists of surgical synechiotomy.

Uterine endoscopic surgery is the standard procedure for surgical synechiotomy. Following this surgery, treatment is performed in which a ovarian hormone preparation (such as estrogen) is administered for the purpose of thickening the endometrium. Although it is said that ovarian hormone stimulate the endometrium resulting in re-epithelialization of wound tissue, there is no definitive evidence of this. In addition, there are patients that are unresponsive even after using estrogen and an article was reported the hormone effect is temporary. Since impairment of the basement membrane of the endometrium or fibrosis of the myometrium occurs if estrogen therapy is not successful, there is also the possibility of the occurrence of circulatory and other disorders.

On the other hand, there is support for the use of intrauterine devices (IUD) following surgery, and in contrast to the adhesion rate being roughly 10% in the case of having used an IUD, adhesion has been reported to occur at roughly 50% in the case of not using an IUD (Non-Patent Document 2). In addition, pregnancy rate among 405 infertile patients that used an IUD was 56%, and 123 (60%) of these cases were reported to be normal pregnancies while 42 cases (27%) ended in miscarriage (Non-Patent Document 1). Although the use of an IUD demonstrates a therapeutic effect, it also contains risks. Since an IUD is ultimately a foreign object, there is the possibility of it not being compatible with tissue as well as having the risk of infection. In addition, there is still the potential for re-adhesion even if an IUD is used.

Remarkable progress has been made in the field of regenerative medicine in recent years, and methods are being sought to regenerate various organs. Research is being conducted on the production of organs that retain a three-dimensional structure by using a bioabsorbable polymer as a scaffold and disseminating cells therein. Although biocompatible scaffolds offer the advantages of facilitating handling and the construction of a three-dimensional structure as a result of being a gel, on the other hand, one of the problems is that animal-derived polymers such as collagen or gelatin contain animal components.

In order to solve such problems, culture methods have recently been developed that use culture dishes coated with a temperature-responsive polymer (Patent Documents 1 to 3). According to this technology, cells are able to be transplanted in the form of a tissue sheet. Cardiac output has previously been confirmed to improve in a canine dilated cardiomyopathy model by transplanting a myoblast sheet (Non-Patent Document 3), and studies are being conducted with the aim of practical application to humans. Although a surgical complication of esophageal mucosal resection in the form of stricture of the excised site becomes a problem in the field of esophageal procedures, this stricture has been demonstrated to be able to be prevented by transplantation of a cell sheet that uses autologous oral mucosa epithelial cells (OMEC) to the excised site (Non-Patent Document 4). In the field of ophthalmology, vision has been demonstrated to be restored following damage to corneal epithelium requiring corneal transplant by transplantation of an autologous oral mucosa epithelial cell sheet (OMECs) (Non-Patent Document 5).

Regenerative medicine research is also being conducted in the fields of obstetrics and gynecology. Examples of this research include research for promoting regeneration of uterine tissue by injecting collagen supplemented with vascular endothelial growth factor (VEGF) (Non-Patent Document 6), research for regenerating uterine tissue using collagen as a scaffold (Non-Patent Document 7), and research for formation of cervical-like tissue using a scaffold made of a silk sponge (Non-Patent Document 8).

PRIOR ART DOCUMENTS

Patent Documents

[Patent Document 1] Japanese Unexamined Patent Publication No. H02-211865
[Patent Document 2] Japanese Unexamined Patent Publication No. H05-192138
[Patent Document 3] Re-publication of PCT International Publication No. 02-008387

Non-Patent Documents

[Non-Patent Document 1] Schenker, J. G. and E. J. Margalioth, Intrauterine adhesions: an updated appraisal, Fertil. Steril., 1982, 37 (5): p. 593-610.
[Non-Patent Document 2] Polishuk, W. Z., A. Adoni and I. Aviad, Intrauterine device in the treatment of traumatic intrauterine adhesions, Fertil. Steril., 1969, 20 (2): p. 241-9.
[Non-Patent Document 3] Hata, H., et al., Grafted skeletal myoblast sheets attenuate myocardial remodeling in pacing-induced canine heart failure model, J. Thorac. Cardiovasc. Surg., 2006, 132 (4): p. 918-924.
[Non-Patent Document 4] Ohki, T., et al., Prevention of esophageal stricture after endoscopic submucosal dissection using tissue-engineered cell sheets, Gastroenterology, 2012, 143 (3): p. 582-8. e1-2.
[Non-Patent Document 5] Nishida, K., et al., Corneal reconstruction with tissue-engineered cell sheets composed of autologous oral mucosal epithelium, N. Engl. J. Med., 351 (12): p. 1187-96.
[Non-Patent Document 6] Lin, N., et al., The effect of collagen-binding vascular endothelial growth factor on the remodeling of scarred rat uterus following full-thickness injury, Biomaterials, 2012, 33 (6): p. 1801-7.
[Non-Patent Document 7] Li, X., et al., Regeneration of uterine horns in rats by collagen scaffolds loaded with collagen-binding human basic fibroblast growth factor, Biomaterials, 2011, 32 (32): p. 8172-81.
[Non-Patent Document 8] House, M., et al., Oxygen tension and formation of cervical-like tissue in two-dimensional and three-dimensional culture, Tissue Eng. Part A, 2012, 18 (5-6): p. 49-507.

DISCLOSURE OF THE INVENTION

Problems to be Solved by the Invention

Conventional organ regeneration research targeted at the remodeling of uterine tissue is currently in the development stage, and any technology for recovery uterine tissue for pregnancy has not yet to be demonstrated. In addition, current therapeutic techniques for intrauterine adhesion still have problems such as the occurrence of re-adhesion and are unable to provide a fundamental solution.

Therefore, in consideration of the aforementioned problems, an object of the present invention is to provide a cell composition for treatment of uterine tissue that heals damage occurring in uterine tissue, including intrauterine adhesion, to a state that enables pregnancy. In addition, an object of the present invention is to provide a method for producing this cell composition for treatment of uterine tissue, and a cell composition for treatment of uterine tissue produced according to that method.

Means for Solving the Problems

The inventors of the present invention conducted research and development in addition to conducting studies from various perspectives in order to solve the aforementioned problems. As a result, it was determined that a cell composition having a first cell layer containing epithelial cells and a second cell layer containing stromal cells, wherein the first cell layer is laminated on the second cell layer, has the ability to heal damage occurring in uterine tissue, including intrauterine adhesion, and restore it to a state that enables pregnancy while undergoing change during the estrus cycle.

Namely, the present invention is as indicated below.

[1] A method for producing a cell composition for treatment of uterine tissue, comprising a step for culturing a cell group containing epithelial cells on a first cell culture support to obtain a first cell layer, a step for culturing a cell group containing stromal cells on a second cell culture support to obtain a second cell layer, and a step for laminating the first cell layer on the second cell layer.

[2] The production method described in [1], wherein the first cell culture support and the second cell culture support have a polymer that undergoes a change in hydration force over a temperature range of 0° C. to 80° C. coated on the surface thereof.

[3] The production method described in [1] or [2], wherein the cell culture side of the first cell culture support is a porous cell insert.

[4] The production method described in [1] to [3], wherein the epithelial cells are derived from uterine tissue.

[5] The production method described in [1] to [4], wherein the epithelial cells are epithelial cells contained in a cell group obtained by a cell separation step for mincing endometrial tissue followed by treating with a cell separation enzyme to obtain an endometrial tissue cell group, a culturing step for disseminating the endometrial tissue cell group on a cell culture vessel and culturing for 30 minutes to 4 hours, and a step for recovering cells that do not adhere to the cell culture vessel after the culturing step.

[6] The production method described in [1] to [5], wherein the stromal cells are endometrial stromal cells.

[7] The production method described in [1] to [6], wherein the stromal cells are endometrial stromal cells contained in a cell group obtained by a cell separation step for mincing endometrial tissue followed by treating with a cell separation enzyme to obtain an endometrial tissue cell group, a culturing step for disseminating the endometrial tissue cell group on a cell culture vessel and culturing for 30 minutes to 4 hours, and a step for recovering the cells that adhere to the cell culture vessel after the culturing step.

[8] A cell composition for treatment of uterine tissue obtained according to the production method described in [1] to [7].

[9] A cell composition for treatment of uterine tissue having a first cell layer composed of a cell group containing epithelial cells, and a second cell layer composed of a cell group containing stromal cells, wherein the first cell layer is layered on the second cell layer, and the side of the bottom layer of the second cell layer retains an adhesive protein.

[10] The cell composition for treatment of uterine tissue described in [9], wherein the epithelial cells are derived from uterine tissue.

[11] The cell composition for treatment of uterine tissue described in [9] or [10], wherein the epithelial cells are endometrial epithelium-like, single layer columnar epithelial cells.

[12] The cell composition for treatment of uterine tissue described in [9] to [11], wherein the stromal cells are derived from uterine tissue.

[13] The cell composition for treatment of uterine tissue described in [9] to [12], wherein the stromal cells are endometrial stromal cells.

[14] The cell composition for treatment of uterine tissue described in [9] to [13], which prevents adhesion following damage to uterine tissue and allows to recover the fertility.

Effect of the Invention

Use of the cell composition indicated in the present invention makes it possible to heal tissue damage occurring in the field of obstetrics and gynecology, and particularly damage occurring in uterine tissue, including intrauterine adhesion, and recover the fertility.

BRIEF DESCRIPTION OF THE DRAWINGS

FIG. 2 indicates tissue sections of an endometrial cell sheet obtained in Example 1. FIG. 2(A) indicates an image obtained by HE staining of the tissue section. FIG. 2(B) indicates an image obtained by immunostaining of the tissue section with a fluorescent-labeled antibody. Red represents vimentin, green represents CK18 and blue represents the location of the cell nucleus.

FIG. 3 indicates images of the uterine tissue of nude rats transplanted with an endometrial cell sheet fabricated in Example 2. The two upper left images indicate the uterus of a normal nude rat, the lower images and upper right image indicate the uterus of a nude rat obtained by transplantation of an endometrial cell sheet into an endometrium full-thickness defect nude rat model, and the tissue sections were stained by HE staining and GFP staining. Arrows indicate the structure of reconstructed endometrial glands.

FIG. 4 is a drawing indicating the flow of an experiment for evaluating pregnancy in the present invention.

FIG. 5(A) depicts the pregnant uterus of a nude rat transplanted the endometrial cell sheet. The endometrial cell sheet was transplanted after causing a full-thickness defect in the endometrium of one of the horns of a bicornuate uterus. The GFP-positive area indicates the transplanted cell sheet, and the gestational sac was able to be confirmed to have been formed at that site. FIG. 5(B) depicts the status of the fetus as determined by ultrasonography. FIG. 5(C) depicts the uterus of an individual not transplanted with a cell sheet after causing a full-thickness defect in the endometrium of one of the horns of a bicornuate uterus.

FIG. 6 indicates cross-sections of pregnant uteri and fetuses of nude rats transplanted with an endometrial cell sheet of Example 3. The three images indicate the respective uterine cross-section of each individual. The areas emitting green fluorescence are the transplanted endometrial cell sheets. Arrows indicate fetuses.

FIG. 7(A) depicts a tissue cross-section of the uterus and fetus following HE staining. FIG. 7(B) depicts the cross-section following GFP and α-SMA immunostaining. The GFP-positive sites indicate the transplanted endometrial cell sheet.

FIG. 8(A) depicts cross-sections of the uterus. FIG. 8(B) depicts partially enlarged views of FIG. 8(A). FIG. 8(C) depicts a site of the endometrium where the cell sheet was transplanted while enlarging a site that is not pregnant.

FIG. 9(A) depicts the uterus of an SD rat transplanted with the endometrial cell sheet. FIG. 9(B) depicts an image observed following irradiation of the same uterus as (A) with a light source that excites GFP. The site emitting green fluorescence is the location of the transplanted cell sheet. FIG. (C) depicts an image observed during ultrasonography of the uterus on the side transplanted with the cell sheet.

FIG. 10(A) depicts an image obtained by HE staining of a uterine tissue section. FIG. 10(B) depicts a horizontal cross-section following GFP immunostaining. The green color indicates the transplanted cell sheet. The blue color indicates the cell nucleus. FIG. 10(C) depicts a coronal cross-section following GFP immunostaining.

FIG. 11 indicates uterine tissue of a nude rat transplanted with an endometrial cell sheet (stromal sheet) of Comparative Example 2. A silicone tube was placed to prevent adhesion of the uterine cavity. FIG. 11(A) depicts the transplanted cell sheet (green fluorescent area). The area indicated with the black circle indicates the silicone tube. FIG. 11(B) depicts the silicone tube immobilized with sutures (arrow).

FIG. 12 indicates the uterine tissue of a nude rat transplanted with an endometrial cell sheet (stromal sheet) of Comparative Example 2. FIG. 12(A) depicts a tissue section following HE staining. In FIG. 12(B), green color indicates the transplanted cell sheet, red color indicates smooth muscle stained with α-SMA antibody, and blue color indicates the cell nucleus. In FIG. 12(C), red color indicates progesterone receptors and blue color indicates the cell nucleus.

BEST MODE FOR CARRYING OUT THE INVENTION

Figure 1:
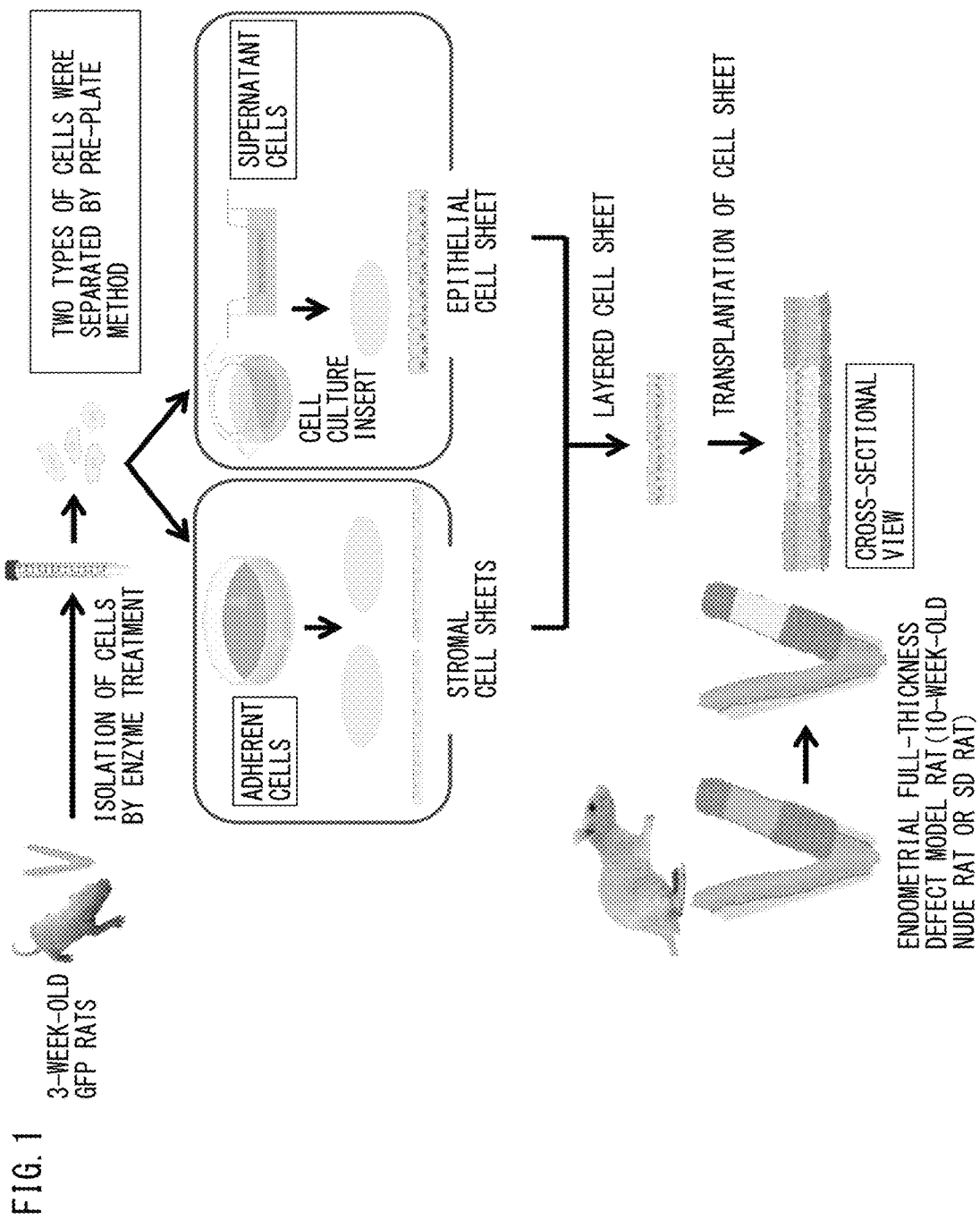
FIG. 1 is a drawing indicating the procedure for fabricating an endometrial cell sheet of the present invention.

The present invention relates to a cell composition for treatment of uterine tissue. In the present invention, a cell composition includes all compositions that contain cells. For example, the cell composition may be a composition to which has been added cells and a protein that composes an extracellular matrix, or may be a composition that contains cells and protein that composes an extracellular matrix produced by the cells, and there are no particular limitations thereon. In addition, the protein that composes the extracellular matrix may be a recombinant protein, or a protein produced from cells incorporated with a gene that encodes that protein or cells that have been transfected with that gene by a vector and the like, and there are no particular limitations thereon.

Uterine tissue refers to tissue of the female reproductive organ of a mammal that serves as an organ for containing a fetus when the fetus develops in the body during pregnancy. In mammals and in humans in particular, uterine tissue has a structure that forms a box-like cavity. The formation of fertilized eggs and the development of the fetus take place in the uterine body. The uterine body is composed of the endometrium, myometrium and parametrium.

The endometrium can be classified into two components based on its tissue structure, and can be divided into the endometrial epithelial layer and endometrial stromal layer. The endometrial epithelial layer is composed of single layer columnar cells, contains secretory cells and ciliated cells, and constitutes the cell layer closest to the uterine cavity. The endometrial stromal layer is a structure that has a large number of endometrial glands. The entrance to the endometrial glands is connected to epithelium facing the uterine cavity, and the innermost portion extends to the deepest portion of the endometrium. Mucus is secreted from the endometrial glands, covers the surface of the endometrium, and assists in the development of fertilized eggs and embryos.

The endometrium can be classified into two layers according to function. These two layers consist of the basal layer, which is located in the deeper portion of the endometrium that does not undergo a change during the estrus cycle, and the functional layer, which undergoes changes in thickness and structure during the estrus cycle and contains the endometrial glands and the coiled artery.

The human endometrium is dependent on female hormones in the form of estrogen and progesterone, and undergoes changes in thickness corresponding to the estrus cycle. Estrogen levels increase during the period from the end of menstruation to ovulation, resulting in proliferation of the endometrium, and particularly the functional layer (proliferative phase). Once ovulation has ended, although estrogen levels temporarily decrease, estrogen levels and progesterone levels subsequently increase again resulting in thickening of the endometrium (secretory phase). At this time, the uterine glands of the endometrium develop and secretion is promoted resulting in the occurrence of edema of the endometrial stromal layer. An environment that is suitable for implantation of a fertilized egg is created in this manner. Subsequently, the menstrual period repeats on a 28 day cycle and exfoliation of the functional layer occurs. At this time, both estrogen and progesterone levels decrease. This thickening and exfoliation of the endometrium according to the estrus cycle fulfills an important role in women for a normal pregnancy.

The cell composition for treatment of uterine tissue of the present invention is a cell composition that has a first cell layer containing epithelial cells and a second cell layer containing stromal cells, and the first cell layer is laminated on the second cell layer. Although epithelial cells include epithelium that covers the body surface, epithelium that composes the mucous membranes of hollow organs, acinar cells that compose exocrine glands and glandular cells that compose endocrine glands, the epithelial cells used in the present invention are preferably cells that compose mucous membranes. Examples thereof include epithelial cells contained in oral mucosa, nasal mucosa, esophageal mucosa and uterine mucosa (endometrium). In particular, epithelial cells derived from uterine tissue are preferable, while the use of epithelial cells derived from the endometrium is more preferable, since they are able to prevent adhesion caused by curettage of uterine tissue and restore uterine tissue to that which undergoes changes corresponding to the estrus cycle or restores uterine tissue to a stage that enables pregnancy. In addition, these epithelial cells may be a single type or may be a mixture of a plurality of types of cells, and there are no particular limitations thereon. In addition, they may also be epithelial cells derived from pluripotent stem cells such as ES cells, iPS cells or Muse cells. The proportion of epithelial cells contained in the first cell layer is 60% or more, preferably 70% or more, more preferably 80% or more and even more preferably 90% or more (such as 90%, 91%, 92%, 93%, 94%, 95%, 96%, 97%, 98%, 99% or 100%). The first cell layer may also contain cells other than epithelial cells, and there are no particular limitations on the types of those cells.

Stromal cells refer to cells that compose the supporting tissue of epithelial cells, and include fibroblasts, vascular endothelial cells, smooth muscle cells and uterine stromal cells. Stromal cells are involved in inflammatory reactions and wound healing reactions, and fulfill an important role in maintaining normal tissue. In the present invention, stromal cells preferably include uterine stromal cells since they allow the obtaining of the effect of preventing adhesion caused by curettage of uterine tissue and restoration of uterine tissue to that which undergoes changes corresponding to the estrus cycle or restoration of uterine tissue to a state that enables pregnancy. In addition, the stromal cells may also be derived from pluripotent stem cells such as ES cells, iPS cells or Muse cells. The proportion of epithelial cells contained in the second cell layer is 60% or more, preferably 70% or more and more preferably 80% or more (such as 80%, 85%, 90%, 95%, 96%, 97%, 98%, 99% or 100%). The second cell layer may also contain cells other than stromal cells, and there are no particular limitations on the types of those cells. In addition, these epithelial cells may be cells of a single type or may be a mixture of a plurality of types of cells.

There are no particular restrictions on the origin of the animal species of the cells used in the present invention, and examples thereof include humans, rats, mice, guinea pigs, marmosets, rabbits, dogs, cats, sheep, pigs, goats, monkeys, chimpanzees and immunodeficient types thereof. It is preferable to use cells derived from humans in the case of using the cell composition of the present invention for the treatment of humans, it is preferable to use cells derived from pigs in the case of using for the treatment of pigs, it is preferable to use cells derived from monkeys in the case of using for the treatment of monkeys, and it is preferable to use cells derived from chimpanzees in the case of using for the treatment of chimpanzees. In addition, in the case the patient undergoing treatment is a human, the cells may be collected from the patient (autologous transplantation), cells may be used that have been collected from another person (allogenic transplantation), or a commercially available cell line may be used.

The cell layers of the present invention refer to a cell group in the form of a sheet composed of one layer or a plurality of layers (such as 2 to 6 layers) obtained by culturing on a cell culture vessel. Although there are no particular limitations on the method used to obtain the cell layers, examples thereof include a method consisting of culturing cells on a cell culture vessel coated with a polymer that undergoes a change in molecular structure due to a stimulus such as temperature, pH or light followed by separating the cells from the surface of the cell culture vessel in the form of a cell layer while maintaining the adhered state between cells by inducing a change in the surface of the cell culture vessel by changing conditions such as the temperature, pH or light, and a method consisting of culturing the cells in an arbitrary cell culture vessel and physically separating the cells from the edge of the cell culture vessel with tweezers and the like. A particularly preferable method consists of culturing cells on a cell culture vessel, which has a polymer coated on the surface thereof that undergoes a change in hydration force over a temperature range of 0° C. to 80° C., within a temperature range at which the hydration force of the polymer is weak, followed by culturing while changing the temperature of the culture broth to a state in which the hydration force of the polymer is strong to separate the cells in the form of a sheet. At that time, the cells are cultured on a cell culture vessel, which is coated on the surface thereof with a polymer that undergoes a change in hydration force over a temperature range of 0° C. to 80° C., within a temperature range in which the hydration force of the polymer is weak. The temperature is preferably a temperature of 37° C. at which cells are normally cultured. The temperature-responsive polymer used in the present invention may be a homopolymer or copolymer. An example of such a polymer is the polymer described in Japanese Unexamined Patent Publication No. H02-211865. More specifically, the polymer is obtained by, for example, homopolymerization or copolymerization of the monomers indicated below. Examples of monomers that can be used include (meth)acrylamide compounds, N- (or N,N-di)alkyl-substituted (meth)acrylamide derivatives and vinyl ether derivatives, and in the case of a copolymer, any two or more of these types can be used. Moreover, copolymerization of monomer types other than those indicated above, graft polymerization or copolymerization of multiple polymers, or a mixture of polymers and copolymers may also be used. In addition, the polymer can also be cross-linked within a range that does not impair the inherent properties of the polymer. At that time, since the target of culturing and separation consists of cells and separation is performed over a temperature range of 5° C. to 50° C., examples of the temperature-responsive polymer include poly(N-n-propylacrylamide) (lower limit critical solution temperature of homopolymer: 21° C.), poly(N-n-propylmethacrylamide) (ditto 27° C.), poly(N-isopropylacrylamide) (ditto 32° C.), poly(N-isopropylmethacrylamide) (ditto 43° C.), poly(N-cyclopropylacrylamide) (ditto 45° C.), poly(N-ethoxyethylacrylamide) (ditto approx. 35° C.), poly(N-ethoxyethylmethacrylamide) (ditto approx. 45° C.), poly(N-tetrahydrofurfurylacrylamide) (ditto approx. 28° C.), poly(N-tetrahydrofurfurylmethacrylamide) (ditto approx. 35° C.), poly(N,N-ethylmethylacrylamide) (ditto 56° C.) and poly(N,N-diethylacrylamide) (ditto 32° C.). Examples of monomers used for copolymerization in the present invention include, but are not limited to, water-containing polymers such as polyacrylamide, poly(N,N-diethylacrylamide), poly(N,N-dimethylacrylamide), polyethylene oxide, polyacrylic acid and salts thereof, poly(hydroxyethyl methacrylate), poly(hydroxyethyl acrylate), polyvinyl alcohol, polyvinylpyrrolidone, cellulose or carboxymethyl cellulose.

There are no particular limitations on the method used in the present invention to coat the culture vessel surface with each of the polymers as previously described, and examples thereof consist of physically adsorbing by coating or kneading and the like the aforementioned monomers or polymers to the vessel by any of electron beam irradiation (EB), γ-ray irradiation, ultraviolet irradiation, plasma treatment, corona treatment or an organic polymerization reaction. The amount of temperature-responsive polymer coated onto the surface of the culture vessel is within the range of 1.2 μg/cm$^2$ to 2.3 μg/cm$^2$, preferably 1.4 μg/cm$^2$ to 1.9 μg/cm$^2$, and more preferably 1.5 μg/cm$^2$ to 1.8 μg/cm$^2$. When the coated amount is less than 1.1 μg/cm$^2$, the cells have difficulty in separating from the polymer even when imparted with a stimulus resulting in a considerable decrease in work efficiency, thereby making this undesirable. Conversely, if the coated amount is 2.3 μg/cm$^2$ or more, cells have difficulty adhering within this range and adequate adhesion of the cells becomes difficult. In such cases, if a cell adhesive protein is further coated onto the temperature-responsive polymer coating layer, the amount of temperature-responsive polymer coated on the vessel surface may be 2.3 μg/cm$^2$ or more, and the coated amount of the temperature-responsive polymer at that time is 9.0 μg/cm$^2$ or less, preferably 8.0 μg/cm$^2$ or less and more preferably 7.0 μg/cm$^2$ or less. If the coated amount of the temperature-responsive polymer is 9.0 μg/cm$^2$ or more, cell adhesion becomes difficult even if a cell adhesive protein is further coated on the temperature-responsive protein coating layer, thereby making this undesirable. There are no particular limitations on the type of cell adhesive protein used, and examples thereof include collagen, laminin, laminin 5, fibronectin and Matrigel either alone or as a mixture of two or more types thereof. In addition, the method used to coat these cell adhesive proteins may be in accordance with a normal method, and a method is normally used in which an aqueous solution of the cell adhesive protein is coated onto the surface of the vessel followed by removing the aqueous solution and rinsing. The present invention constitutes a technology that attempts to use a cell sheet per se that utilizes a temperature-responsive culture dish. Thus, the coated amount of cell adhesive protein on the temperature-responsive polymer layer is preferably not excessively large. The coated amount of the temperature-responsive polymer and the coated amount of the cell adhesive protein may be measured in accordance with normal methods, and examples of methods that may be used include any of a method consisting of measuring a portion where cells are adhered directly using FT-IR-ATR, and a method consisting of immobilizing a preliminarily labeled polymer using a similar method and estimating the coated amount from the amount of labeled polymer immobilized by a portion where cells are adhered.

In the method of the present invention, although varying according to the animal species of the cells used, the number of cells disseminated during culturing is typically $0.2 \times 10^6$ to $10 \times 10^6$ cells/cm$^2$, preferably $0.3 \times 10^6$ to $9 \times 10^6$ cells/cm$^2$, and more preferably $0.4 \times 10^6$ to $8 \times 10^6$ cells/cm$^2$. In the present invention, in order to separate and recover the cultured cell sheet from the temperature-responsive culture vessel, the cultured cell sheet can be separated by making the temperature of the culture vessel adhered with cultured cells to be equal to or higher than the upper limit critical solution temperature or equal to lower than the lower limit critical solution temperature of the coated polymer. At that time, the cultured cell sheet can be separated in the culture broth or other isotonic solution, and can be selected according to the objective. A method consisting of gently tapping or shaking the culture vessel, stirring the medium using a pipette, or using a tweezers may be used alone or in combination for the purpose of separating and recovering the cells more quickly and with greater efficiency. Culturing conditions other than temperature may be in accordance with ordinary methods and there are no particular limitations thereon. For example, the medium used may be a medium containing a known serum such as fetal bovine serum (FBS), or may be a serum-free medium to which such serum has not been added.

The following provides an explanation of the preceding matters using the example of poly(N-isopropylacrylamide) for the temperature-responsive polymer. Poly(N-isopropylacrylamide) is known to be a polymer that has a lower limit critical solution temperature at 31° C., and if put into the free state, undergoes dehydration at a temperature of 31° C. or higher in water resulting in coagulation of the polymer chain that causes it to become turbid. Conversely, at a temperature of 31° C. or lower, the polymer chain is hydrated and enters a state in which it is dissolved in water. In the present invention, this polymer is coated and immobilized on the surface of a Petri dish or other culture vessel. Thus, if the temperature is equal to higher than 31° C., although the polymer on the surface of the culture vessel similarly undergoes dehydration, since the polymer chain is coated and immobilized on the surface of the culture vessel, the surface of the culture vessel becomes hydrophobic. Conversely, if the temperature is equal to or lower than 31° C., although the polymer on the surface of the culture vessel is hydrated, since the polymer chain is coated and immobilized on the surface of the culture vessel, the surface of the culture vessel becomes hydrophilic. The hydrophobic surface at this time is a surface that is suitable for the adhesion and proliferation of cells, while the hydrophilic surface prevents cells from adhering thereto, thereby resulting in cultured cells or a cell sheet being separated simply by cooling.

Glass, modified glass and compounds such as polystyrene or polymethacrylate used in ordinary cell culturing, as well as substances typically capable of imparting a shape, such as polymer compounds other than those listed above and ceramics, can all be used for the culture vessel that is subjected to coating.

There are no particular limitations on the form of the cell culture vessel used in the present invention, and examples thereof include a dish, multi-plate, flask or cell insert cultured on a porous membrane as well as that having a flat shape. In the case the cultured cells are epithelial cells, the use of a cell insert enables culture broth to make contact above and below the cells resulting in layering of the cells, thereby making this preferable. Examples of the cell culture vessel that is subjected to coating include glass, modified glass and compounds such as polystyrene or polymethacrylate used in ordinary cell culturing, as well as substances typically capable of imparting a shape, such as polymer compounds other than those listed above and ceramics.

The cell sheet used in the present invention is not subjected to damage by proteases represented by dispase or trypsin during culturing. Consequently, the cell sheet separated from the cell culture vessel has adhesive protein, and when cells have been separated in the form of a sheet, the desmosome structures between cells are maintained to a certain degree. As a result, the cells can be favorably adhered when placing on vascular bed and are able to take efficiently. Although the typical protease, dispase, is known to be able to cause separation in a state in which 10% to 40% of the desmosome structures between cells are maintained, since nearly all basal membrane-like proteins between the cells and culture vessel end up being destroyed, the resulting cell sheet has weak strength. In contrast, the cell sheet of the present invention is able to obtain the various effects as previously described as a result of being in a state in which 60% or more of the desmosome structures and basal membrane-like proteins remain intact.

There are no particular limitations on the method used to fabricate the cell composition having a plurality of cell layers in the present invention, and examples of methods for obtaining the cell composition include a method consisting of disseminating cells in a cell culture vessel and coating a gel containing a protein composing an extracellular matrix protein (such as laminin, collagen, gelatin, cadherin, hyaluronic acid, fibronectin, fibrin, elastin, chitin, chitosan or hydronectin) thereon, followed by further seeding cells to obtain a layered cell composition, and a method consisting of separating cultured cells in the form of a sheet and layering a plurality of cultured cell sheets using a cultured cell transfer tool as necessary. There are no particular limitations on the temperature at that time provided that, in the case the aforementioned polymer coated on the surface of the culture vessel has an upper limit critical solution temperature, it is equal to or lower than that temperature, or in the case the aforementioned polymer has a lower limit critical solution temperature, it is equal to or higher than that temperature. However, it goes without saying that culturing at an excessively low temperature range that prevents the cultured cells from proliferating, or an excessively high temperature range that causes the cultured cells to die, is unsuitable. Culturing conditions at a temperature other than those temperatures may be performed in accordance with ordinary methods and there are no particular limitations thereon. For example, the medium used may be a known medium to which serum has been added such as fetal bovine serum, or may be a serum-free medium to which serum has not been added. In addition, a tool may be used as necessary to transfer the cell sheet. Although there are no particular limitations whatsoever on the material or shape of the tool provided it is able to grasp the separated cell sheet, examples of materials of the tool include polyvinylidene fluoride (PVDF), silicon, polyvinyl alcohol, urethane, cellulose and derivatives thereof, chitin, chitosan, collagen, gelatin and fibrin sealant, and the tool is used by contacting the cell sheet while in the form of a film, porous film, nonwoven fabric or woven fabric.

The cell composition obtained in the present invention can be transplanted to a prescribed site in the body. At that time, vascularization may be preliminarily induced at the transplant site, and there are no particular limitations thereon. Here, although there are no particular limitations on the method used to induce vascularization, and examples of methods thereof include a method consisting of embedding a vascular growth factor in the form of FGF in a microsphere, and allowing to act in the body for 8 to 10 days while changing the composition, size and injection range of the microsphere, and a method consisting of cutting a polyethylene terephthalate mesh to an arbitrary size, forming the mesh into the shape of a bag, placing FGF dissolved in a highly concentrated agarose solution inside the bag and removing the bag after 8 to 10 days to create a space in which vascularization has been induced.

EXAMPLES

Although the following provides a more detailed explanation of the present invention based on examples thereof, these examples do not limit the present invention in any way. Furthermore, the experimental protocols using rats of the examples were approved by the ethics committee relating to animal experiments of the Tokyo Women's Medical University, and were implemented in accordance with the "Guide for the Care and Use of Laboratory Animals" (1996 edition) published by the U.S. National Institute of Health (NIH).

(Animals)

Fabrication of cell sheets: Three-week-old GFP rats (strain: SD-Tg (CAG-EGFP), Japan SLC, Inc.) and SD rats (strain: S1c:SD, Japan SLC, Inc.) were purchased and euthanized with $CO_2$.

Transplanted animals: Nine-week-old nude rats (strain: F344/NJcl-rnu/rnu, CLEA Japan, Inc.) were purchased and used for transplant at age 10 weeks.

The animals were anesthetized with 4% isoflurane and maintained at about 1.8%. Hypothermia was prevented by using a hot plate during the procedure. The regenerated uterus and damaged uterus rats were sacrificed by exsanguination following deep anesthesia. When extracting fetuses from pregnant individuals, the mothers were sacrificed by placing under deep anesthesia, and the fetuses and mothers were sacrificed by the same method. At that time, a longer duration of anesthesia than normal was used for the fetuses in consideration of their higher tolerance to hypoxia.

(Fabrication of Cell Sheets)

The method used to fabricate cell sheets is indicated in FIG. 1. More specifically, 3-week-old SD rats or GFP rats were laparotomized to confirm the uterus. The ligament connecting the ovaries on both sides with the pelvis was dissected and the cervix was resected after spreading open the mesometrium followed by extracting the uterus. Subsequently, the extracted uterus was separated into the myometrium and endometrium under a microscope. The separated endometrial tissue was treated for 20 minutes in a mixture of 0.25% trypsin and 0.1% EDTA at 37° C. while shaking at 150 bpm. Following treatment, the mixture was pipetted about 70 to 100 times with a 5 mL pipette and then about 200 times with a 1000 μm Pipetman. This was performed until the mixture was visually confirmed to be free of aggregates as an indicator of completion. After terminating the reaction with an equal amount of medium containing 10% FBS, the mixture was filtered with 100 μm and 40 μm cell strainers. The acquired cells were completely disseminated into a 100 mm dish and allowed to stand undisturbed for 2 hours (to be referred to as the "cell sorting step"). Two hours later, the supernatant was collected and washed three times with PBS. The PBS used during washing was also collected. This supernatant and the washed cells were combined and designated as (1). After washing, the cells remaining in the dish were allowed to react for 5 minutes at 37° C. in a mixture of 0.25% trypsin and 0.1% EDTA and then collected. The collected cells were designated as (2). The cells of (1) were seeded on an insert immobilized with a temperature-responsive polymer at $5.0 \times 10^6$ cells/dish, and the cells of (2) were seeded on a 35 mm temperature-responsive culture dish (Upcell®, CellSeed Inc.) at $2.5 \times 10^6$ cells/dish. The cells of (1) were cultured using DMEM/F12 medium containing 10 μg/mL of insulin, 10 μg/mL of transferrin, 0.038 μM selenite, 100 μg/mL of hydrocortisone, 2.5 nM retinoic acid, 100 μM ascorbic acid and 10 ng/mL of EGF. The cells of (2) were cultured using DMEM/F12 medium (1:1) containing 10% FBS, 1% penicillin, 1% streptomycin and 1% Hepes. Four days after seeding, the cells seeded in the insert were separated from the wall surfaces by tracing the periphery of the insert over the entire circumference using a 200 μm chip. The cells seeded in the culture dish were separated from the wall surfaces by tracing the periphery of the dish over the entire circumference about 6 times using a 1000 μm chip. Both cells were subsequently harvested as cell sheets by incubation for 1 hour at 20° C. The cell sheet of (1) was separated with tweezers in cases in case of difficult to separate. The separated cell sheets were suspended in medium and PBS. The sheet of (1) was transferred to an ordinary culture dish and suspended therein. Subsequently, a plastic sheet measuring about 1 cm×1 cm was first placed under the cell sheet of (2) in the culture dish in which the cell sheet of (2) was suspended, followed by spreading the cell sheet over the plastic sheet by removing the medium. The spread cell sheet was placed in a culture dish, in which another cell sheet was suspended, together with the plastic sheet, and placed under the suspended second cell sheet. The second sheet was then spread over the plastic sheet so as to form a two-layer laminated state by removing the medium in the same manner as the first sheet. A three-layer laminated sheet was then fabricated by spreading the cell sheet of (2) over the cell sheet of (1) on the two-layer laminate using the same method (resulting in a laminate having three cell sheets in the order of (1), (2) and (2) from the top).

Example 1

(In Vitro Evaluation of Layered Sheets)

The layered cell sheets were placed on an ordinary insert (Falcon) and spread out by removing the medium. 2 mL of medium (DMEM/F12 (1:1) containing 10% FBS, 1% penicillin, 1% streptomycin and 1% Hepes) were placed in a 6-well plate. The layered cell sheets were then incubated for 3 days at 37° C. and 5% $CO_2$ while in that state. Subsequently, the cell sheets were immobilized to a re-adhesive sheet in the form of 4% PFA while adhered to the membrane of the insert.

(Tissue Evaluation and Immunostaining Evaluation)

The cell sheets were embedded in paraffin, cut into thin sections and subjected to HE staining. Immunostaining was performed by activating using a pressure cooker using a pH 6 activator. Subsequently, blocking was performed for 2 hours with 10% goat serum. Following blocking, primary antibody such as GFP, CK18 or vimentin was allowed to react overnight at a ratio of 1:100 and 4° C. Secondary antibody was subsequently allowed to react for 1 hour at room temperature to perform nuclear staining followed by mounting.

As shown in FIG. 2, the upper portion of the cell sheet of (1) was observed to uniformly consist of CK18-positive cells expressed in epithelial cells, while vimentin-positive cells were confirmed on the opposite side on the side of the surface of the culture dish. The cell sheet of (2) consisted of cells negative for CK18 and positive for vimentin. The layered cell sheet was confirmed to have a single layer of CK18-positive cells in the upper portion thereof immediately after layering, and vimentin-positive cells present under CK-18 positive layer were confirmed. However, gaps were confirmed between the sheets. A single layer of CK18-positive cells was also confirmed in the upper portion of the re-adhesive sheet, and although a vimentin-positive layer was confirmed there below, gaps were not confirmed.

Example 2

(Cell Sheet Transplantation)

Ten-week-old nude rats were laparotomized to expose the uterus. The uterus was then opened by making a longitudinal incision. The myometrium and endometrium were physically separated using tweezers under a microscope. The range of separation was targeted at a distance of 1 cm in the center of the uterus. After separating the endometrium and leaving only the myometrium, the uterus was stitched 5 points each on the left and right from both sides using 7-0 Nylon sutures and positioned at the transplant site so as to spread out on both sides. Subsequently, hemostasis was performed using a heated scalpel. The layered cell sheet in the manner described above was transplanted directly to the transplant site from the plastic sheet used during layering. Subsequently, wet gauze was placed around the transplant site and a 100 mm tissue cover was placed thereon to prevent drying. The cell sheet was allowed to take by remaining undisturbed for 1.5 hours while in that state. After taking, the extended Nylon sutures were removed and the transplant site was closed by continuously suturing with 7-0 absorbable sutures. A group was simultaneously prepared as a control group in which the myometrium and endometrium were physically separated followed by closing without transplanting a cell sheet.

(Evaluation of Regenerated Uterus)

The regenerated uterus was evaluated 4 weeks after transplanting the cell sheet. The uterus was observed using small animal ultrasonography. The transplanted uterus was observed moving from the cervical canal towards the Fallopian tube to confirm the presence or absence of constricted sites. In addition, confirmation was also made as to the presence or absence of edema-like changes in the direction of the Fallopian tube. Constriction and obstruction were suspected in the case the presence of cystic changes was confirmed. Moreover, the uterus was injected with physiological saline to confirm the presence or absence of obstruction. The rat vagina was extended using an otolaryngological auditory canal observation instrument to expose the cervical canal. The mantle of a 22 G intravenous indwelling needle was inserted uterine cavity through the cervical canal while guided by ultrasonography. Following insertion, physiological saline was injected while observing by ultrasonography. Following injection, the uterus was judged to be free of obstruction if the entire uterus extended uniformly. Obstruction was judged to be present in the case the physiological saline did not flow in the direction of the Fallopian tubule. In the case of obstruction, the length of the obstructed site was measured by ultrasonography. Moreover, an observation was made as to whether or not GFP-positive sites can be confirmed by laparotomizing under anesthesia. In addition, an evaluation was made as to the presence or absence of cystic changes. The control group was also evaluated for the presence or absence of edema-like changes, and the endometrium separation site was confirmed to have thinned. Following confirmation, the 7-0 absorbable sutures used to suture the uterus were removed. The uterus was extracted together with the control group in order to evaluate the regenerated uterus 4 weeks after transplantation. The wounds of individuals used as pregnant uteri were performed synechiotomy against postoperative adhesion from around the uterus.

The uterus at four weeks after transplantation was observed a luminal structure that was equivalent to a normal structure on the inner side of the myometrium, and endometrial gland structures were observed in the stromal layer (FIG. 3). In addition, GFP-positive tissue was observed, and CK18 and GFP positive cells were lined for shape the luminal structure. In the control group, there was hardly any tissue observed within the tissue of the myometrium, while regeneration of uterine tissue was prominently confirmed in the transplant group.

Example 3

(Mating and Evaluation of Pregnancy)

FIG. 4 indicates the flow of an experiment for mating and evaluation of pregnancy. More specifically, female nude rats were housed with male nude rats in the same cages at 2 weeks after evaluation of the regenerated uterus by laparotomizing. The abdomens of the animals were observed using small animal ultrasonography under anesthesia 2 weeks after the start of cohabitation. Judgement of establishment of pregnancy was confirming gestational sac and fetus by ultrasonography. Individuals in which at least one fetus was confirmed in the normal right side uterus or either the transplanted or damaged left uterus were judged to be pregnant individuals. Individuals in which a gestational sac and fetus were unable to be clearly confirmed but were suspected of being pregnant (due to changes in uterine structure) were reevaluated several days later and were judged to be pregnant individuals based on the aforementioned criteria. Those animals that did not become pregnant were housed with a different individual and then reevaluated. This procedure was repeated until pregnancy was successful. Pregnant individuals were laparotomized at the stage they were diagnosed as being pregnant followed by macroscopic and fluorescence microscope observations of the uterus. The uterus was subsequently extracted and fixed with 4% PFA. Three days after fixation, the gestational sac was cut into horizontal cross-sections and the cross-sections were observed with a light microscope and fluorescence microscope. The cross-sections were again fixed with 4% PFA following observation.

(Evaluation of Gravid Uterus)

Figure 5:
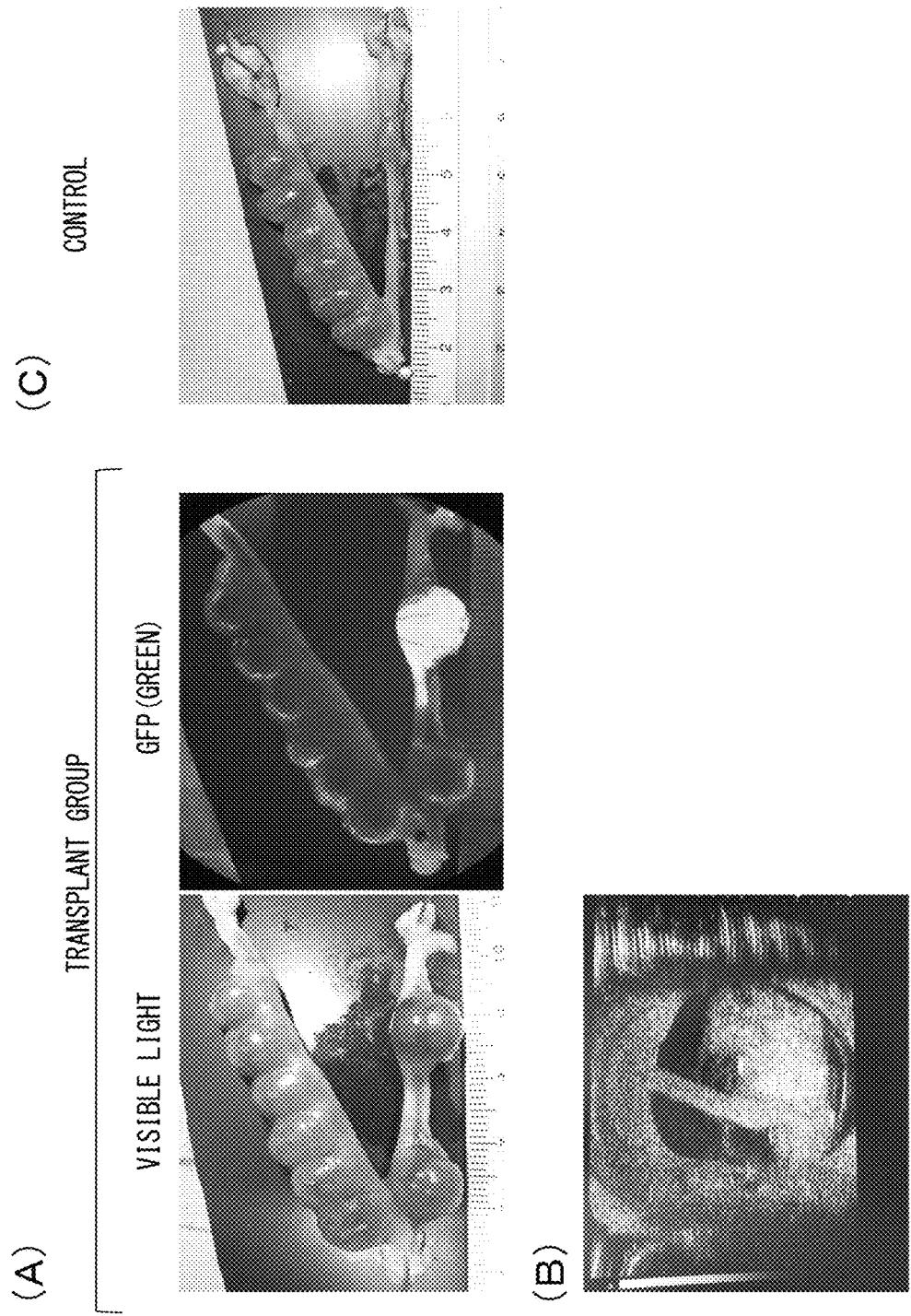
FIG. 5 indicates the fertility restorative effect of an endometrial cell sheet of Example 3.
Figure 7:
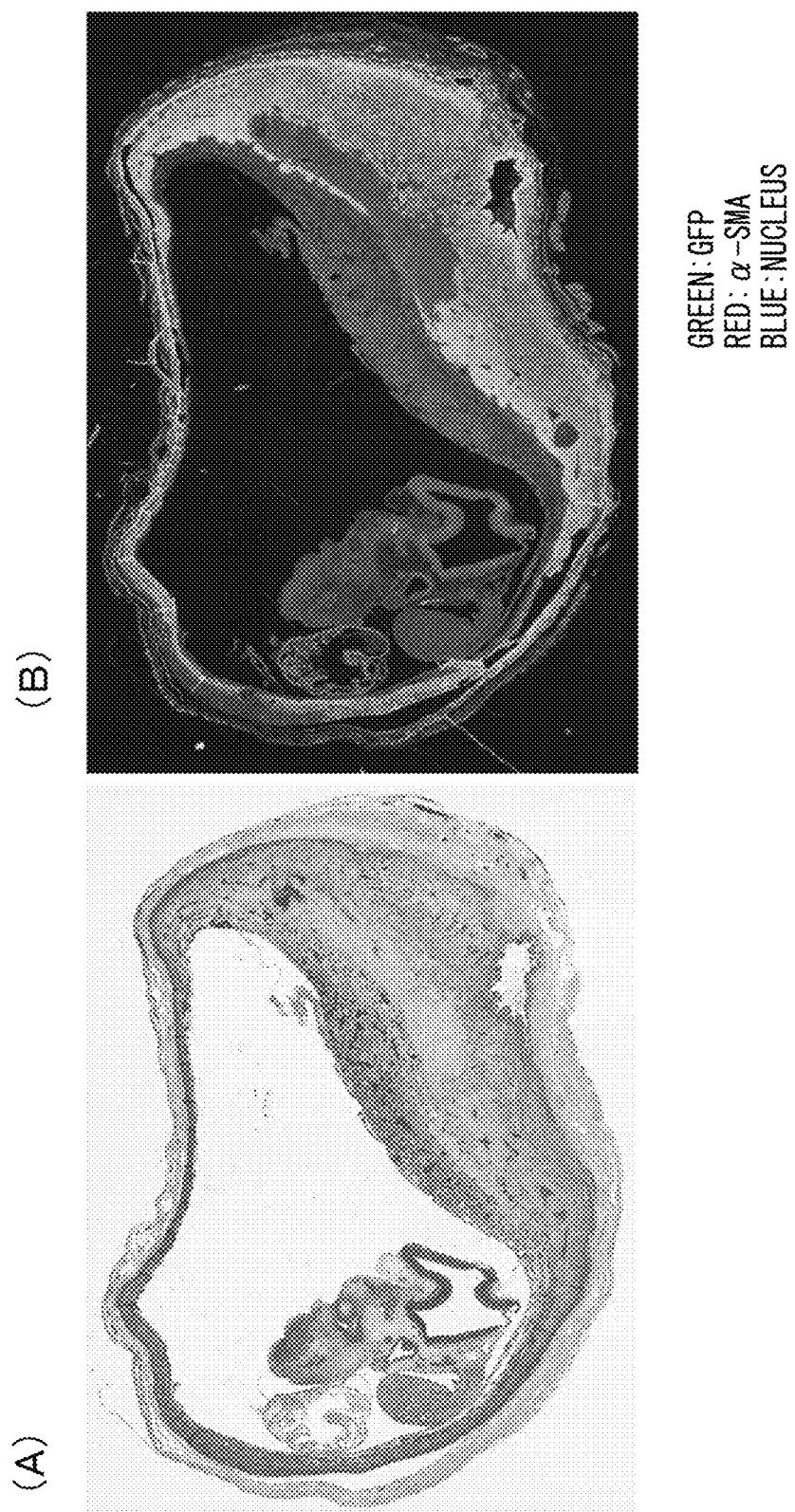
FIG. 7 indicates tissue sections of the uterus and fetus of a nude rat transplanted with an endometrial cell sheet of Example 3.
Figure 8:
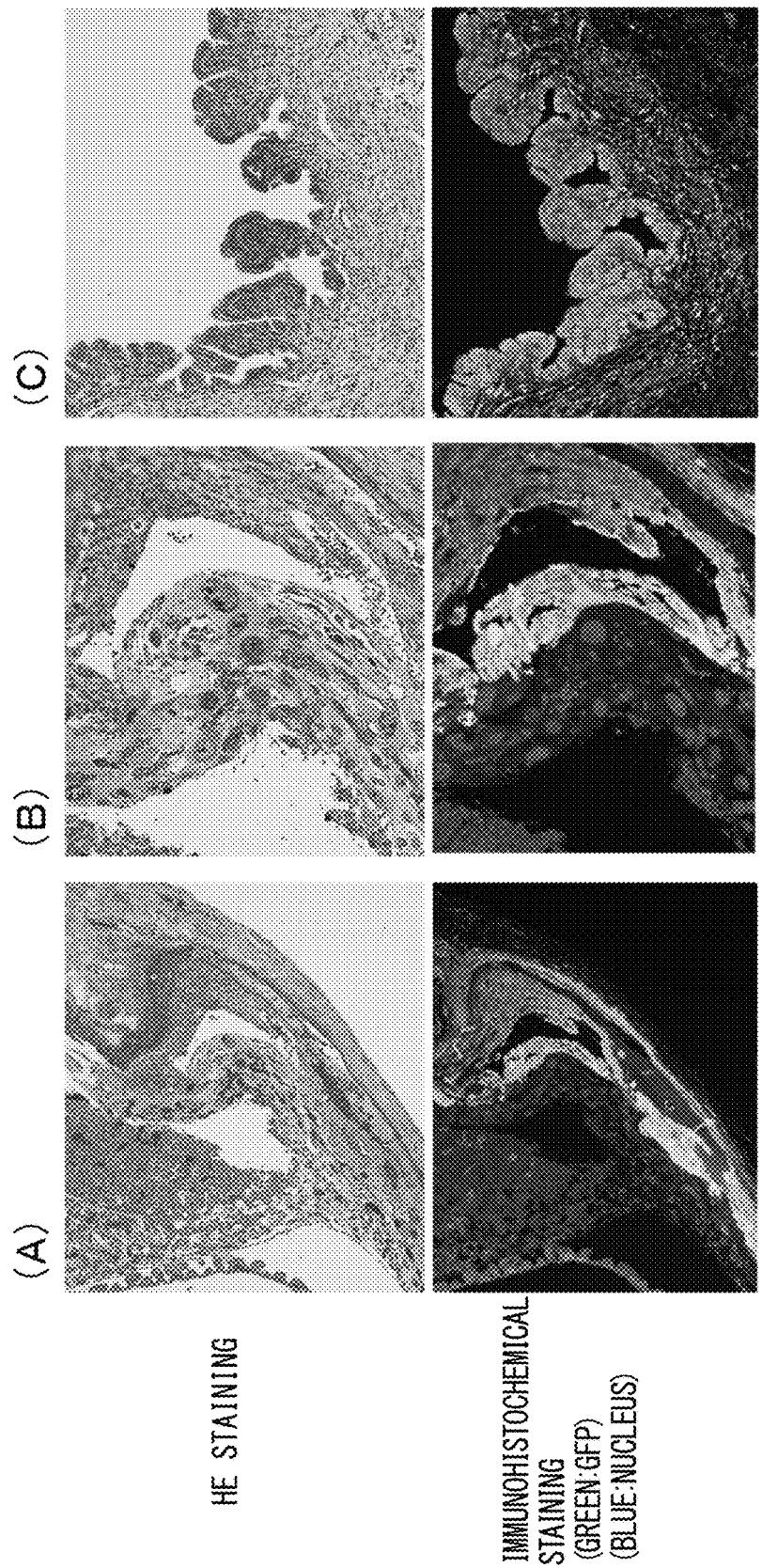
FIG. 8 indicates uterine tissue sections of a nude rat transplanted with an endometrial cell sheet of Example 2. The upper row indicates images obtained by HE staining, while the lower row indicates images obtained by GFP immunostaining.

In the pregnant uteri, 70% to 90% of the gestational sacs were confirmed GFP-positive sites in the cell sheet transplantation group (FIG. 5). In horizontal cross-sections, GFP-positive sites were confirmed over the entire outer circumference of the gestational sac, and GFP-positive sites were confirmed over a wide range directly beneath the placenta (FIG. 6). GFP-positive sites were similarly confirmed over the entire outer circumference of the gestational sac and GFP-positive sites were confirmed over a wide range directly beneath the placenta in tissue specimens as well (FIG. 7). In addition, GFP-positive endometrial epithelium was confirmed at non-pregnant sites as well, and an Arias-Stella reaction (reaction in which the endometrium changes to a papillary shape due to the effects of pregnancy) was observed based on the shape thereof (FIG. 8). On the basis thereof, the endometrial cell sheet was confirmed to change accompanying pregnancy following transplantation.

Example 4

(Evaluation of Endometrial Cell Sheet Derived from Allogenic Origin)

Figure 9:
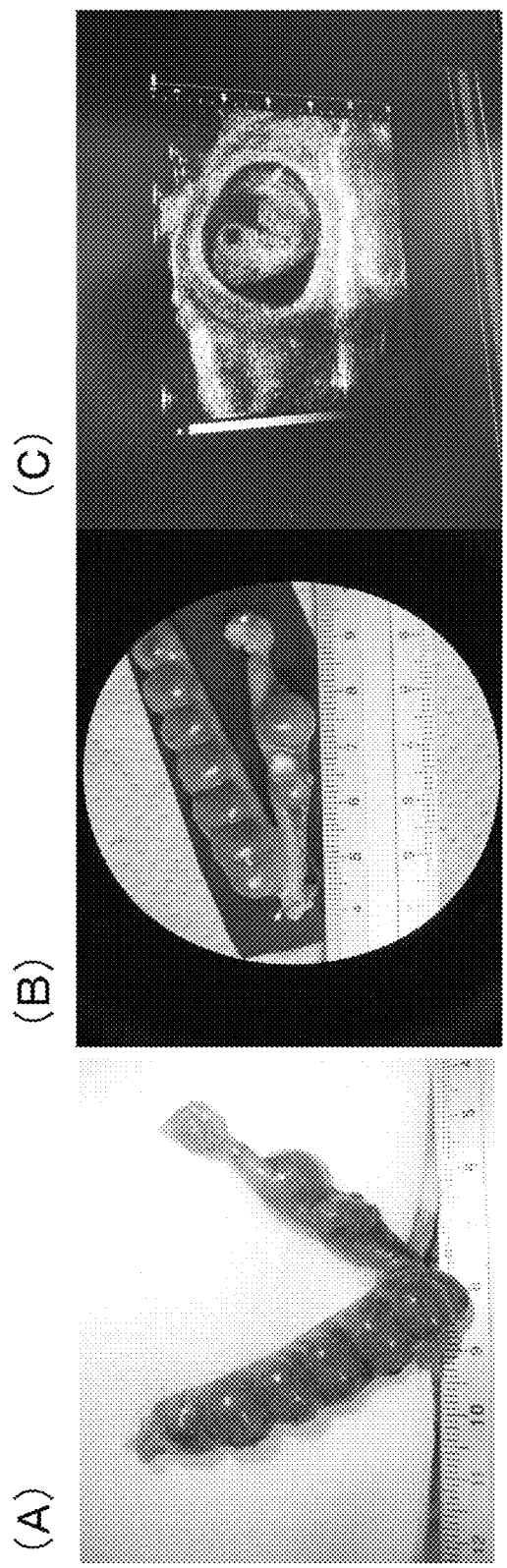
FIG. 9 indicates the fertility restorative effect of transplanting an endometrial cell sheet of Example 4.

The same experiment as Example 3 was performed with the exception of using rats having a normal immune response in the form of SD rats for the experimental animals followed by evaluating whether or not they are able to become pregnant by transplant animals. As a result, the endometrial cell sheets were able to take and pregnancy was confirmed to be possible even in the case of using rats having a normal immune response in the form of SD rats for the transplanted animals (FIG. 9).

Comparative Example 1

(Evaluation of Uterus Regenerative Effects of Uterine Stromal Cell Sheet)

Figure 10:
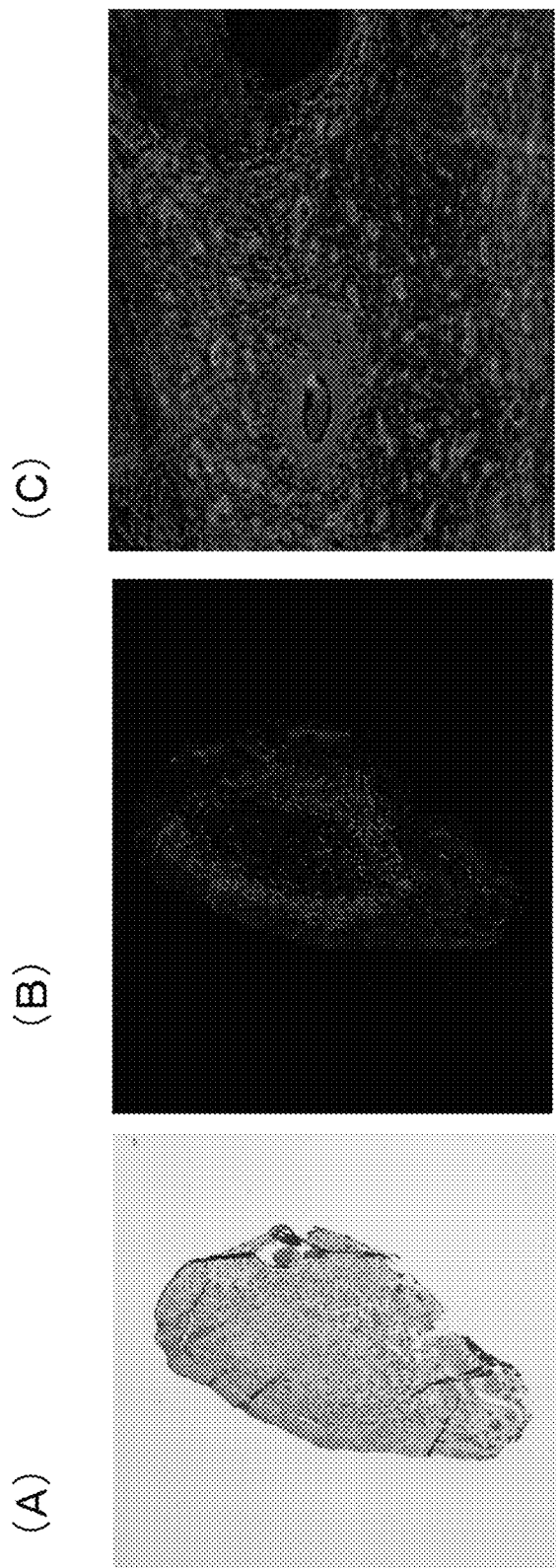
FIG. 10 indicates uterine tissue of a nude rat transplanted with an endometrial cell sheet of Comparative Example 1.

Since the uterine stromal cell sheet also contains epithelial cells, a study was conducted as to whether or not uterus regenerative effects are demonstrated with only a uterine stromal cell sheet. The experiment was conducted using the same methods as Example 2 and Example 3 with the exception of using cell sheets derived from adherent cells for all cell sheets layered in the cell sorting step of the method used to fabricate the cell sheets. As a result, although the transplanted cell sheets were confirmed engraftment, adhesion at the wound site was unable to be prevented, and the uterine cavity was not confirmed (FIG. 10). In addition, pregnancy was also not confirmed.

Comparative Example 2

(Evaluation of Uterus Regenerative Effects of Transplantation of Uterine Stromal Cell Sheet and Silicone Tube Placement)

A study was conducted as to whether or not luminal structure is maintained and the epithelial layer is reconstructed by placing a silicone tube simultaneous to transplanting a uterine stromal cell sheet. A uterine stromal cell sheet was transplanted into the uterus of nude rats from which the endometrium had been removed in the same manner as Comparative Example 1, followed by the placement of a silicone tube (AS ONE Corp.) and suturing (FIG. 11). One week after transplantation, uterine tissue sections were prepared followed by HE staining and immunostaining in accordance with established methods. As a result, the structure of the uterine cavity was maintained, cells derived from the cell sheet were confirmed, and cells positive for progesterone receptors specifically expressed in the endometrium were confirmed (FIG. 12(C)). However, a large number of inflammatory cells were observed at sites contacted by the silicone tube, while epithelial cells were not found.

All publications and patent documents cited in the present description are incorporated in the present description in their entirety by reference. Furthermore, although specific embodiments of the present invention have been explained in the present description for the purpose of exemplification, it is easily understood by a person with ordinary skill in the art that the present invention may be modified in various ways without deviating from the spirit and scope thereof.

The invention claimed is:

1. A method for producing a cell composition for treatment of uterine tissue, the method comprising:
   (1) culturing a cell group containing epithelial cells on a first cell culture support to obtain a first cell layer, and then recovering the first cell layer from the first cell culture support;
   (2) culturing a cell group containing stromal cells on a second cell culture support to obtain a second cell layer, and then recovering the second cell layer from the second culture support; and
   (3) laminating the first cell layer on the second cell layer, wherein:
   the first cell culture support and the second cell culture support have a polymer that undergoes a change in hydration force over a temperature range of 0° C. to 80° C. coated on the surface thereof; and
   the epithelial cells are derived from uterine tissue.

2. The production method according to claim 1, wherein the first cell culture support is a porous cell culture insert.

3. The production method according to claim 1, wherein the epithelial cells are epithelial cells contained in a cell group obtained by:
   (1) a cell separation step for mincing endometrial tissue followed by treating with a cell separation enzyme to obtain an endometrial tissue cell group,
   (2) a culturing step for seeding the endometrial tissue cell group on a cell culture vessel and culturing for 30 minutes to 4 hours, and
   (3) a step for collecting cells that do not adhere to the cell culture vessel after the culturing step.

4. The production method according to claim 1, wherein the stromal cells are endometrial stromal cells.

5. The production method according to claim 1, wherein the stromal cells are endometrial stromal cells contained in a cell group obtained by:
   (1) a cell separation step for mincing endometrial tissue followed by treating with a cell separation enzyme to obtain an endometrial tissue cell group,
   (2) a culturing step for seeding the endometrial tissue cell group on a cell culture vessel and culturing for 30 minutes to 4 hours, and
   (3) a step for collecting the cells that adhere to the cell culture Vessel after the culturing step.

* * * * *